(12) United States Patent
Bonde et al.

(10) Patent No.: US 9,539,421 B2
(45) Date of Patent: Jan. 10, 2017

(54) MEDICAL DEVICE ANCHORING APPARATUS AND METHODS

(71) Applicant: Medtronic, Inc., Minneapolis, MN (US)

(72) Inventors: Eric H. Bonde, Minnetonka, MN (US); Mark J. Holle, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 282 days.

(21) Appl. No.: 13/795,441

(22) Filed: Mar. 12, 2013

(65) Prior Publication Data
US 2014/0155909 A1 Jun. 5, 2014

Related U.S. Application Data

(60) Provisional application No. 61/733,584, filed on Dec. 5, 2012.

(51) Int. Cl.
*A61B 17/00* (2006.01)
*A61N 1/05* (2006.01)
(Continued)

(52) U.S. Cl.
CPC ............ *A61N 1/0539* (2013.01); *A61M 25/04* (2013.01); *A61B 17/3468* (2013.01);
(Continued)

(58) Field of Classification Search
CPC ....... A61B 19/20; A61B 16/201; A61B 19/22; A61B 1/0539; A61B 19/203
(Continued)

(56) References Cited

U.S. PATENT DOCUMENTS

| | | | |
|---|---|---|---|
| 5,464,446 A | | 11/1995 | Dreessen et al. |
| 5,843,150 A | * | 12/1998 | Dreessen ............. A61N 1/0529 128/898 |

(Continued)

FOREIGN PATENT DOCUMENTS

| | | |
|---|---|---|
| EP | 1016432 A2 | 7/2000 |
| GB | 2344054 A | 5/2000 |

(Continued)

OTHER PUBLICATIONS

The International Search Report and The Written Opinion, PCT/US2013/073429, Jul. 24, 2014, 19 pages.
(Continued)

*Primary Examiner* — Tuan V Nguyen
(74) *Attorney, Agent, or Firm* — Mueting, Raasch & Gebhardt, P.A.

(57) ABSTRACT

Methods and apparatus for anchoring an elongate medical device within a body portal, for example, a stimulation lead in a cranial burr hole, employ a securing element attached to a plate member, which may be held over a body portal by a base ring. The securing element includes a spring member and an engagement surface; a retaining member holds the engagement surface, spaced apart from a side of a slot of the plate member, in an open position, against a bias of the spring member. In the open position, the device may be received between the engagement surface and the side of the slot, through an opening of the slot. Disengaging the retaining member releases a moveable portion of the spring member to move the engagement surface toward the side of the slot and into a closed position, at which the inserted device is anchored. The anchored device may be routed through one of a plurality of base ring channels.

12 Claims, 11 Drawing Sheets

(51) Int. Cl.
  *A61M 25/04* (2006.01)
  *A61M 25/02* (2006.01)
  *A61B 17/34* (2006.01)
  *A61N 1/36* (2006.01)
  *A61M 5/00* (2006.01)

(52) U.S. Cl.
  CPC ........... *A61B 17/3472* (2013.01); *A61B 90/11* (2016.02); *A61B 2017/347* (2013.01); *A61B 2034/301* (2016.02); *A61B 2034/302* (2016.02); *A61B 2090/103* (2016.02); *A61M 5/00* (2013.01); *A61M 2025/024* (2013.01); *A61N 1/36025* (2013.01); *A61N 2001/36039* (2013.01)

(58) Field of Classification Search
  USPC ........................................................ 606/130
  See application file for complete search history.

(56) References Cited

U.S. PATENT DOCUMENTS

| | | | |
|---|---|---|---|
| 5,865,842 | A | 2/1999 | Knuth et al. |
| 5,927,277 | A | 7/1999 | Baudino et al. |
| 5,954,687 | A | 9/1999 | Baudino |
| 6,044,304 | A | 3/2000 | Baudino |
| 6,134,477 | A | 10/2000 | Knuteson |
| 6,210,417 | B1 | 4/2001 | Baudino et al. |
| 6,214,016 | B1 | 4/2001 | Williams et al. |
| 6,321,104 | B1 | 11/2001 | Gielen et al. |
| 6,902,569 | B2 | 6/2005 | Parmer et al. |
| 7,033,326 | B1 | 4/2006 | Pianca et al. |
| 7,177,701 | B1 | 2/2007 | Pianca |
| 7,204,840 | B2 | 4/2007 | Skakoon et al. |
| 7,235,084 | B2 | 6/2007 | Skakoon et al. |
| 7,346,391 | B1 | 3/2008 | Osorio et al. |
| 7,421,297 | B2 | 9/2008 | Giftakis et al. |
| 7,580,756 | B2 | 8/2009 | Schulte et al. |
| 7,588,581 | B2 | 9/2009 | Solar et al. |
| 7,604,644 | B2 | 10/2009 | Schulte et al. |
| 7,604,655 | B2 | 10/2009 | Warnick |
| 7,637,915 | B2 | 12/2009 | Parmer et al. |
| 7,704,260 | B2 | 4/2010 | Skakoon et al. |
| 8,050,772 | B1 * | 11/2011 | Daglow et al. ............... 607/116 |
| 8,738,151 | B2 * | 5/2014 | Nelson ........................ 607/116 |
| 2002/0052610 | A1 * | 5/2002 | Skakoon ............... A61B 19/201 606/129 |
| 2005/0015128 | A1 | 1/2005 | Rezai et al. |
| 2005/0054985 | A1 | 3/2005 | Mogg |
| 2005/0143800 | A1 | 6/2005 | Lando et al. |
| 2005/0182420 | A1 | 8/2005 | Schulte et al. |
| 2005/0182421 | A1 | 8/2005 | Schulte et al. |
| 2005/0182422 | A1 | 8/2005 | Schulte et al. |
| 2005/0182423 | A1 * | 8/2005 | Schulte ................ A61N 1/0539 606/130 |
| 2005/0182424 | A1 | 8/2005 | Schulte et al. |
| 2005/0182425 | A1 | 8/2005 | Schulte et al. |
| 2005/0182464 | A1 | 8/2005 | Schulte et al. |
| 2005/0192594 | A1 | 9/2005 | Skakoon et al. |
| 2007/0233158 | A1 | 10/2007 | Rodriguez |
| 2007/0249980 | A1 | 10/2007 | Carrez et al. |
| 2008/0017206 | A1 | 1/2008 | Becker et al. |
| 2008/0172068 | A1 | 7/2008 | Adams et al. |
| 2009/0088826 | A1 | 4/2009 | Bedenbaugh |
| 2009/0112327 | A1 | 4/2009 | Lane et al. |
| 2009/0118804 | A1 | 5/2009 | Moffitt et al. |
| 2009/0187149 | A1 | 7/2009 | Nelson |
| 2009/0259186 | A1 | 10/2009 | Smith et al. |
| 2010/0023100 | A1 | 1/2010 | Barker |
| 2010/0145357 | A1 | 6/2010 | Lane et al. |
| 2010/0280585 | A1 | 11/2010 | Appenrodt et al. |
| 2011/0238040 | A1 | 9/2011 | Johnson et al. |
| 2012/0010626 | A1 | 1/2012 | Daglow et al. |
| 2012/0316628 | A1 | 12/2012 | Lopez |
| 2014/0155859 | A1 | 6/2014 | Bonde et al. |
| 2014/0155860 | A1 | 6/2014 | Behymer et al. |

FOREIGN PATENT DOCUMENTS

| | | |
|---|---|---|
| WO | 2005079903 A2 | 9/2005 |
| WO | 2008054691 A2 | 5/2008 |
| WO | 2009055746 A2 | 4/2009 |
| WO | WO 2014/089360 A2 | 6/2014 |
| WO | WO 2014/089366 A2 | 6/2014 |
| WO | WO 2014/089371 A2 | 6/2014 |

OTHER PUBLICATIONS

The International Search Report and The Written Opinion, PCT/US2013/073419, Jul. 2, 2014, 19 pages.
The International Search Report and The Written Opinion, PCT/US2013/073439, Aug. 28, 2014, 16 pages.
Guardian Cranial Burr Hole Cover System, Clinician's Manual, ANS, Apr. 2009.
Invitation to Pay Additional Fees and Patel Search Report, PCT/US2013/073436, Apr. 10, 2014, 6 pgs.
PCT Patent Application No. PCT/US2013/073419, filed Dec. 5, 2013; International Preliminary Report on Patentability issued Jun. 18, 2015; 12 pages.
PCT Patent Application No. PCT/US2013/073419, filed Dec. 5, 2013; Invitation to Pay Additional Fees and Communication Relating to the Results of the Partial International Search issued Apr. 9, 2014, 7 pages.
PCT Patent Application No. PCT/US2013/073429, filed Dec. 5, 2013; International Preliminary Report on Patentability issued Jun. 18, 2015; 13 pages.
PCT Patent Application No. PCT/US2013/073429, filed Dec. 5, 2013; Invitation to Pay Additional Fees and Communication Relating to the Results of the Partial International Search issued Feb. 27, 2014, 6 pages.
PCT Patent Application No. PCT/US2013/073436, filed Dec. 5, 2013; International Preliminary Report on Patentability issued Jun. 18, 2015; 10 pages.
U.S. Appl. No. 13/795,458; Office Action issued May 7, 2015; 13 pages.
U.S. Appl. No. 13/795,458; Office Action issued Oct. 8, 2015; 8 pages.
U.S. Appl. No. 13/795,458; Advisory Action issued Dec. 17, 2015; 3 pages.
U.S. Appl. No. 13/795,490; Office Action issued Sep. 18, 2015. 11 pages.
U.S. Appl. No. 13/795,490; Office Action issued Mar. 8, 2016. 11 pages.
U.S. Appl. No. 13/795,458, filed Mar. 12, 2013, Bonde et al.
U.S. Appl. No. 13/795,490, filed Mar. 12, 2013, Behymer et al.
Dictionary definition of "press fit" as provided by PTO with Mar. 8, 2016 Office Action in U.S. App. No. 13/795,490, [indicated by PTO as being retrieved on Mar. 2, 2016]. Retrieved from the Internet: <URL:http://dictionary.reference.com/browse/press-fit>, 2 pages.

* cited by examiner

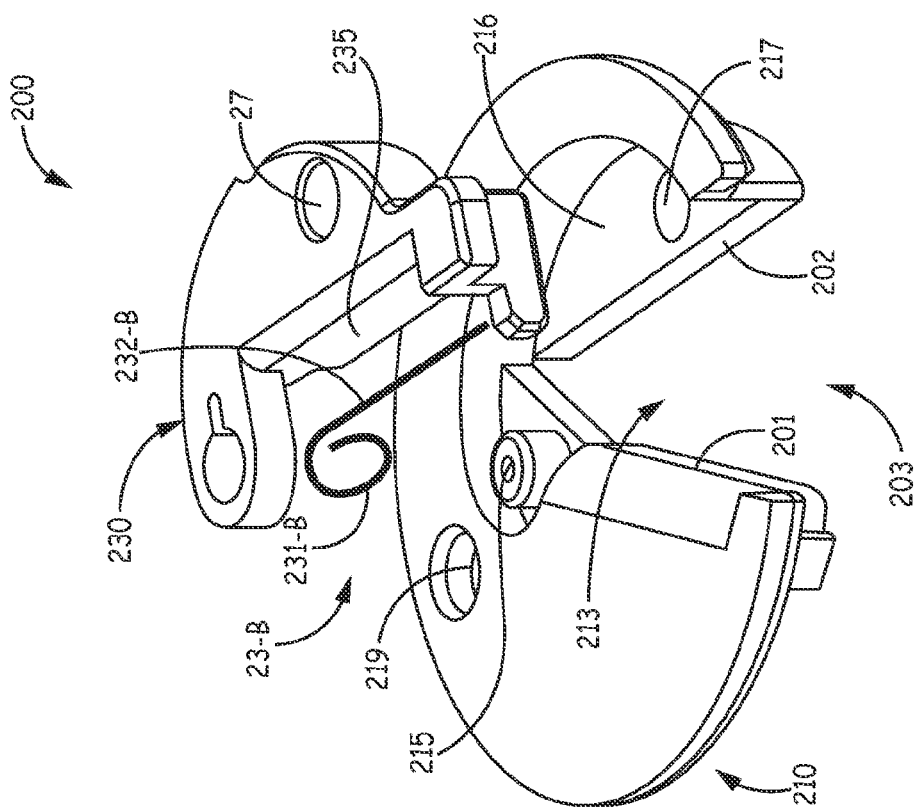
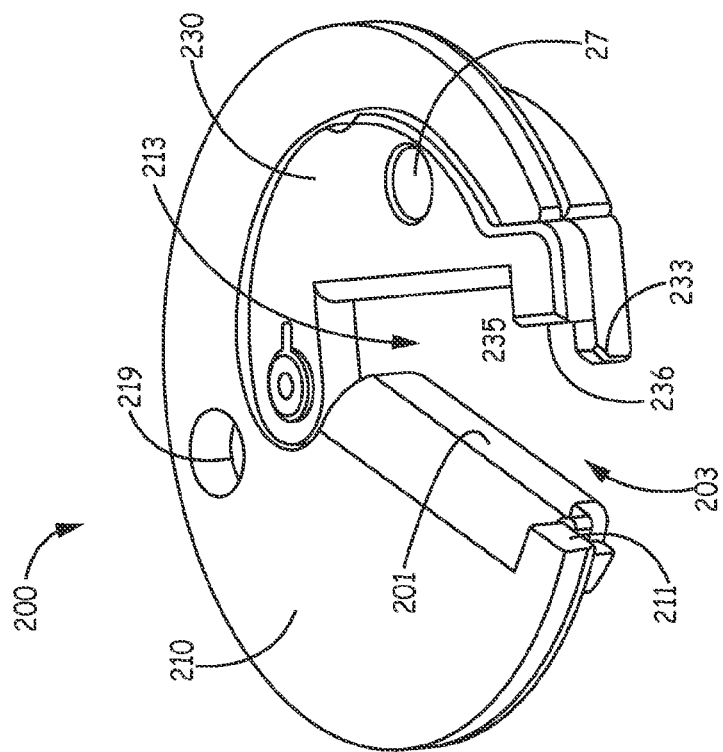

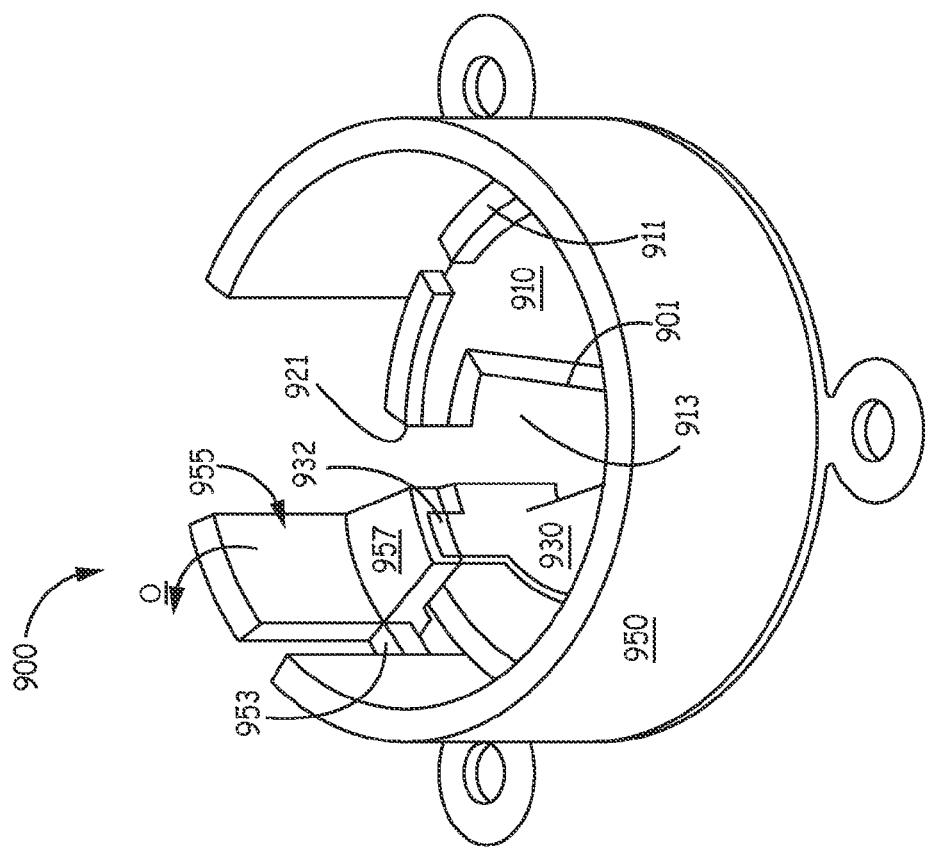
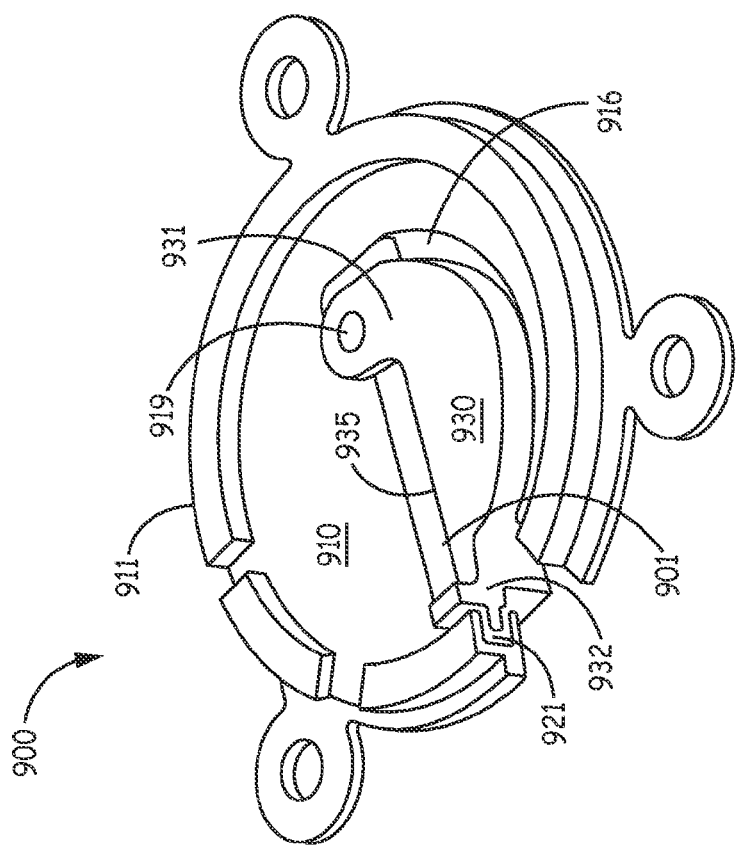
FIG. 4F
FIG. 4E

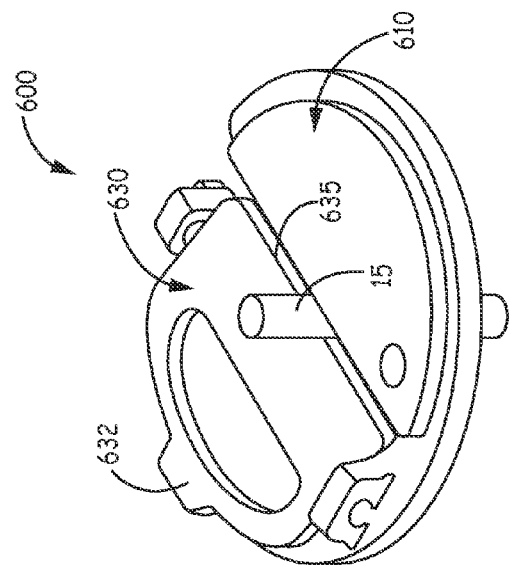
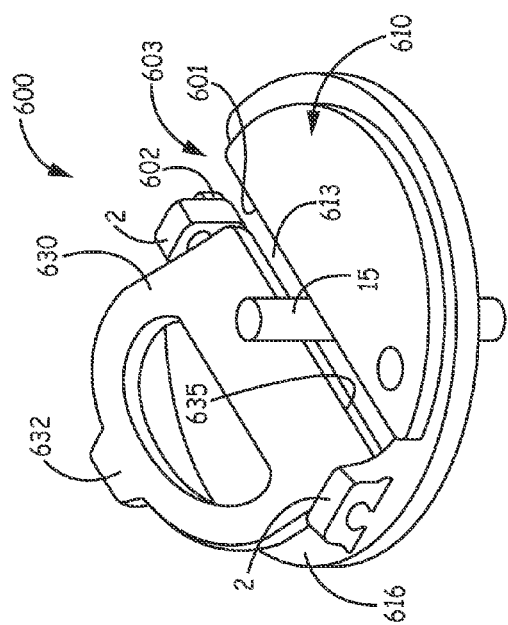
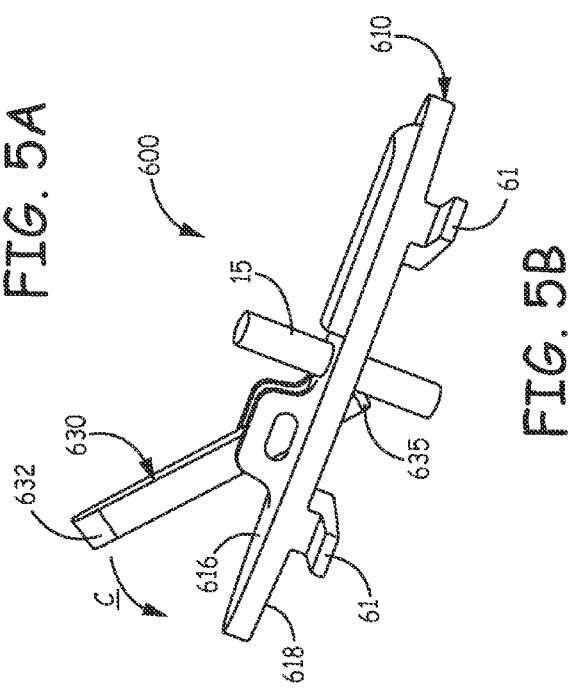
FIG. 5C
FIG. 5A
FIG. 5B

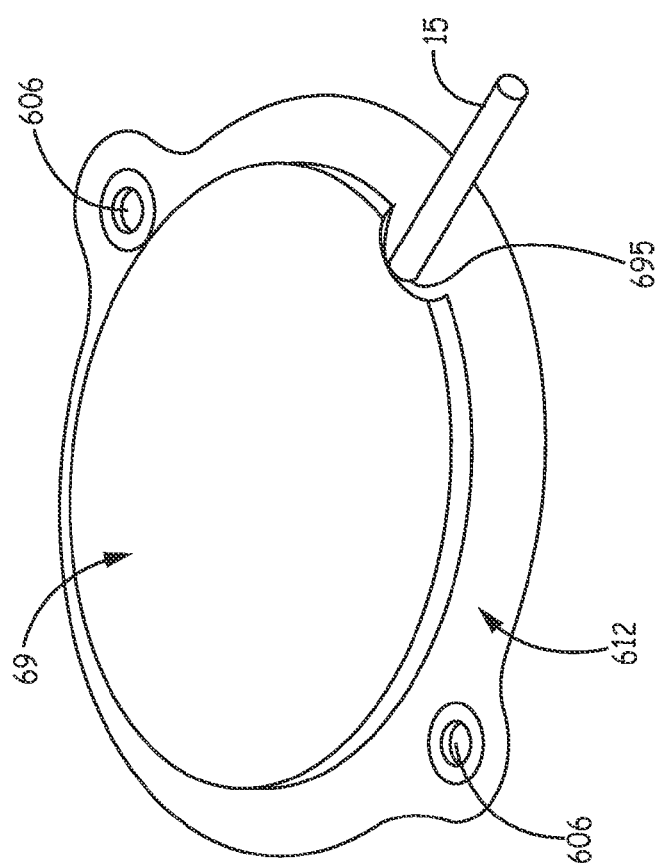
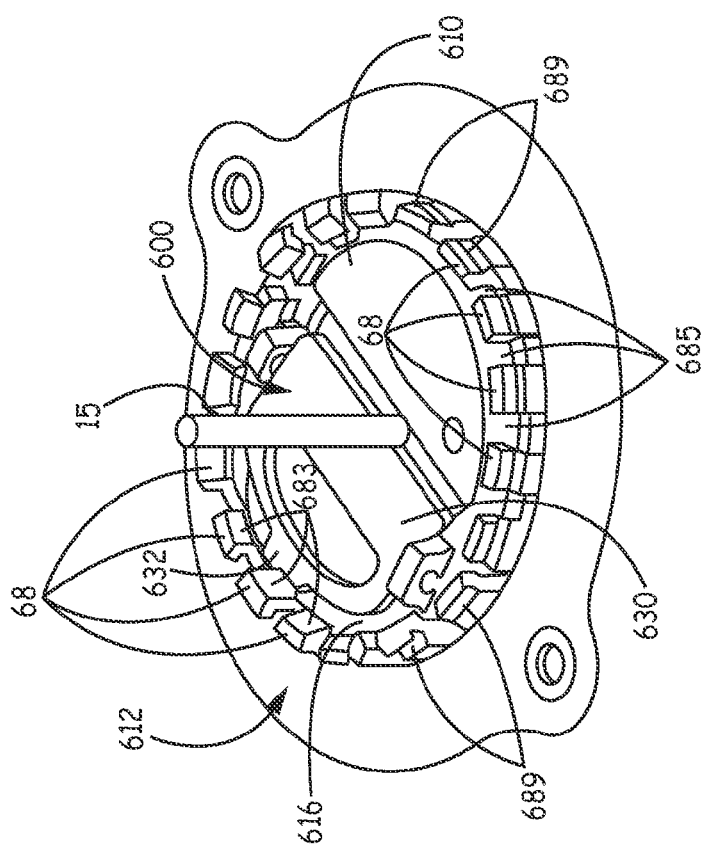
FIG. 5E
FIG. 5D

MEDICAL DEVICE ANCHORING APPARATUS AND METHODS

CROSS-REFERENCE TO RELATED APPLICATIONS

The present application claims priority to U.S. Provisional Patent Application Ser. No. 61/733,584, which was filed on Dec. 5, 2012, and is hereby incorporated by reference in its entirety. The present application is related to the following commonly assigned and co-pending U.S. Non-provisional patent applications, filed concurrently herewith and having the same title as the instant application, each of which is hereby incorporated by reference in its entirety: U.S. patent application Ser. No. 13/795,490, and U.S. patent application Ser. No. 13/795,458.

TECHNICAL FIELD

The present disclosure pertains to medical devices and more particularly to various apparatus, assemblies and methods for anchoring an elongate medical device within a body portal, for example, a burr hole formed in a skull of a patient.

BACKGROUND

Medical procedures for treating a variety of neurological conditions, for example, Parkinson's disease, essential tremor and dystonia, require access to the brain, typically through a burr hole formed in the skull, for the insertion of deep brain stimulating electrodes. Burr holes may also be formed for the insertion of a delivery catheter, for example, to provide drug therapy for similar conditions. Stereotactic apparatus and procedures, which are known to those skilled in the art, may be employed by surgeons to locate inserted electrodes and/or drug delivery ports in target regions of the brain.

FIG. 1A is a perspective view of an exemplary stereotactic guidance system 100 (e.g. Medtronic Nexdrive Micropositioning Drive attached to the Medtronic Nexframe®) mounted to a patient's skull. FIG. 1A illustrates a ring 120 of guidance system 100, which extends around a perimeter of a burr hole 11 formed in the skull, supporting a socket assembly 140 to which a micropositioning drive 160 is attached. Burr hole 11 may be fitted with a base ring 112 (FIG. 1B; e.g. the Medtronic Stimloc base) that is mounted around burr hole 11 prior to attaching ring 120 of guidance system 100. FIG. 1 further illustrates an elongate medical device 15, for example, a medical electrical lead carrying one or more stimulating electrodes, held within drive 160 for advancement through burr hole 11 and into the target region of the brain.

FIG. 1B illustrates a portion of the implanted device 15, after guidance system 100 is removed, extending proximally out from base ring 112, which lines burr hole 11, and which is fastened to the skull, for example, via screws received through holes 106 in base ring 112. Those skilled in the art appreciate that a proximal portion of implanted device 15, outside the cranial space, may be routed, beneath the scalp and subcutaneously, to a therapy generator (not shown), for example, implanted in proximity to the clavicle. FIG. 1B further illustrates device 15 extending through a slot of base ring 112 so that device 15 may be secured/anchored between base ring 112 and a cap that snaps into place thereover (not shown; e.g. the Medtronic Stimloc cap). Although various configurations of apparatus for securing elongate medical devices in body portals, such as burr holes, are known in the art, there is still a need for new and improved anchoring apparatus and methods, for example, to increase the ease by which anchoring is activated, without dislodging the implanted device, and without compromising the stability of anchoring.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 3A-B are a perspective view, and an exploded perspective view of an anchoring assembly, according to some additional embodiments;

FIG. 4E is a perspective view of an anchoring assembly, according to some additional embodiments;

FIG. 4F is a perspective view a retaining member engaged with the anchoring assembly of FIG. 4E, according to some embodiments;

FIGS. 5A-B are perspective views of an anchoring assembly, according to some alternate embodiments; and FIGS. 5C-E are perspective views of the assembly including a base ring, according to some embodiments.

DETAILED DESCRIPTION

Embodiments of anchoring assemblies, disclosed herein, are suitable for mounting/fixing in or over a body portal, for example, a cranial burr hole, in order to anchor in place an implanted elongate medical device, such as an electrical lead or a fluid delivery catheter, which is implanted in the body via insertion through the body portal. The assemblies include various configurations of a securing element attached to a plate member, wherein the securing element includes a spring member and an engagement surface, to which a moveable portion of the spring member is coupled. The engagement surface of each embodiment may be retained in an open position, by a corresponding retaining member, while the elongate medical device is inserted between the engagement surface and an opposing side of a slot of the plate member, and then moved to a closed position, via release of the moveable portion of the spring member, in order to anchor the inserted device. Some embodiments of separate base rings that may be included in anchoring assemblies are also disclosed herein. Associated methods for employing the various apparatus and assemblies are disclosed in conjunction with the detailed description of each embodiment. The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 2A:
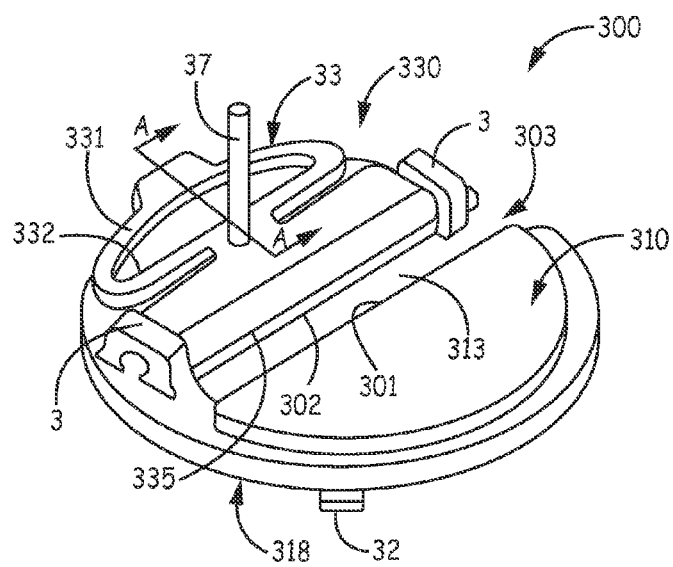
FIG. 2A is a perspective view of an anchoring assembly, according to some embodiments.
Figure 2B:
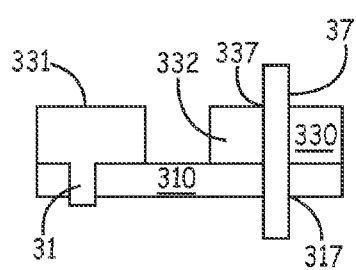
FIG. 2B is a cross-section view corresponding to section line A-A of FIG. 2A, according to some embodiments.

FIG. 2A is a perspective view of an anchoring assembly 300, and FIG. 2B is a cross-section view corresponding to section line A-A of FIG. 2A, according to some embodiments. FIG. 2A illustrates assembly 300 including a plate member 310, generally defining a plane, and a securing element 330 overlaying a surface 316 of plate member 310, and attached to plate member 310, for example, by mounting features 3 of plate member 310, and by an interlocking projection 31 of element 330, which may be seen in FIG. 2B. Assembly 300 may be fitted within a base ring which lines, or surrounds a body portal, for example, base ring 112 described above, and may be held in place by engagement within an inner perimeter of the base ring, for example, by detent features 32 that are shown extending from a lower surface 318 of plate member 310, which is opposite surface 316. FIG. 2A further illustrates plate 310 including a slot 313 having opposing sides 301, 302 that extend generally along the plane defined by plate member 310 from a slot opening 303, at a perimeter of plate member 310. Plate member 310 may be formed, for example, by molding, from a biocompatible polymer such as polyurethane, polycarbonate, polysulfone, PEEK, or nylon.

With further reference to FIGS. 2A-B, securing element 330 includes an engagement surface 335 and a spring member 33, wherein spring member 33 includes a first portion 331 fixed to plate member 310, and a second, moveable portion 332 coupled to engagement surface 335. Engagement surface 335 of securing element 330 is shown in an open position, extending in proximity to side 302 of slot 313 and spaced apart form side 301 of slot 313 by a distance that allows insertion of an elongate medical device into slot 313, via opening 303, for example, a proximal portion of implanted lead 15 that extends proximally out from a body portal (e.g., cranial burr hole 11), prior to fitting assembly 300 into the aforementioned base ring 112. With reference to the cross-section of FIG. 2B, a retaining member 37, in the form of a pin member, passes through a hole 337 of securing element 330 and through an underlying hole 317 of plate member 310 to hold moveable portion 332 of spring member 33 against a bias of spring member 33, that is, in compression with respect to a fixed portion 331 of spring member 33, to keep engagement surface 335 in the open position. Securing element 330 may be formed from a biocompatible metal material, for example, stainless steel, or, preferably, nitinol, for MRI compatibility, but may alternately be formed from a biocompatible polymer material that has the necessary spring/elastic properties.

Figure 2C:
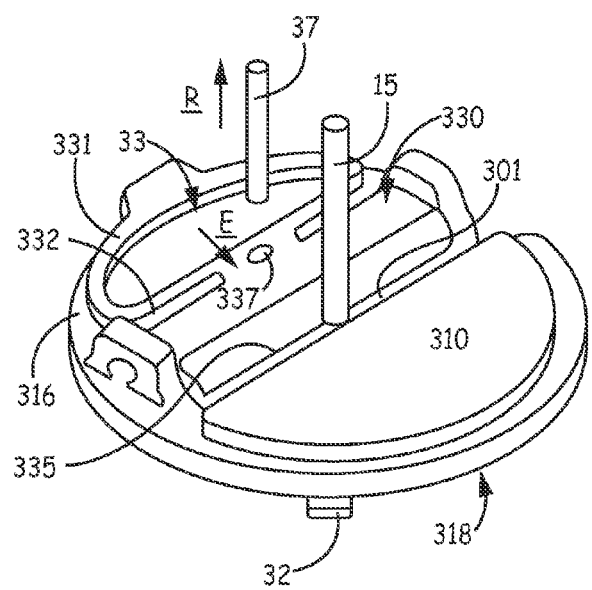
FIG. 2C is another perspective view of the anchoring assembly of FIG. 2A, according to some embodiments.

FIG. 2C is another perspective view of the anchoring assembly of FIG. 2A, according to some embodiments, after inserting the proximal portion of lead 15 into slot 313 and disengaging pin member 37 from holes 337, 317, for example, per arrow R. According to the illustrated embodiment, the disengagement of pin member 37 releases moveable portion 332 of spring member 33 thereby allowing an expansion of spring member 33, which moves engagement surface 335 of securing element 330 per arrow E, to a closed position, at which engagement surface 335 anchors lead 15 against side 301 of slot 313. Engagement surface 335 preferably includes a groove formed along a length thereof and/or a textured surface for enhancing the gripping of lead 15; furthermore each of engagement surface 335 and first side 301 of slot 313 preferably have rounded edges. With further reference to FIGS. 2A and 2C, engagement surface 335 extends approximately parallel to side 301 of slot in the open position, and, when moveable portion 332 of spring member 33 is released, the direction (arrow E) in which surface 335 moves is approximately orthogonal to side 301.

According to some alternate methods, a pre-positioned delivery catheter, through which lead 15 is delivered to the target region of the brain, may be inserted into slot 313, via opening 303, prior to disengaging pin member 37 to release moveable portion 332 of spring member 33; thus, engagement surface 335 may hold the catheter in position, against side 301 of slot 313, while lead 15 is delivered therethrough for implantation. Then, upon removal of the catheter from slot 313, and over implanted lead 15, spring member 33 further expands to move engagement surface 335 of securing element 330 in the closed position to anchor lead 15 against side 301 of slot 313.

FIGS. 3A-B are a perspective view, and an exploded perspective view of an anchoring assembly 200, according to some alternate embodiments. FIGS. 3A-B illustrate anchoring assembly 200 including a plate member 210, which generally defines a plane, and a securing element 230, which is pivotably attached to plate member 210 at a post 215 thereof, and overlays a surface 216 of plate member 210. FIGS. 3A-B further illustrate plate member 210 including a slot 213 having opposing sides 201, 202 that extend generally along the defined plane of plate member 210 from a slot opening 203, at a perimeter of plate member 210. Plate member 210 and securing element 230 may each be formed, for example, by molding, from a biocompatible polymer such as polyurethane, polycarbonate, polysulfone, PEEK, or nylon.

Figure 3C:
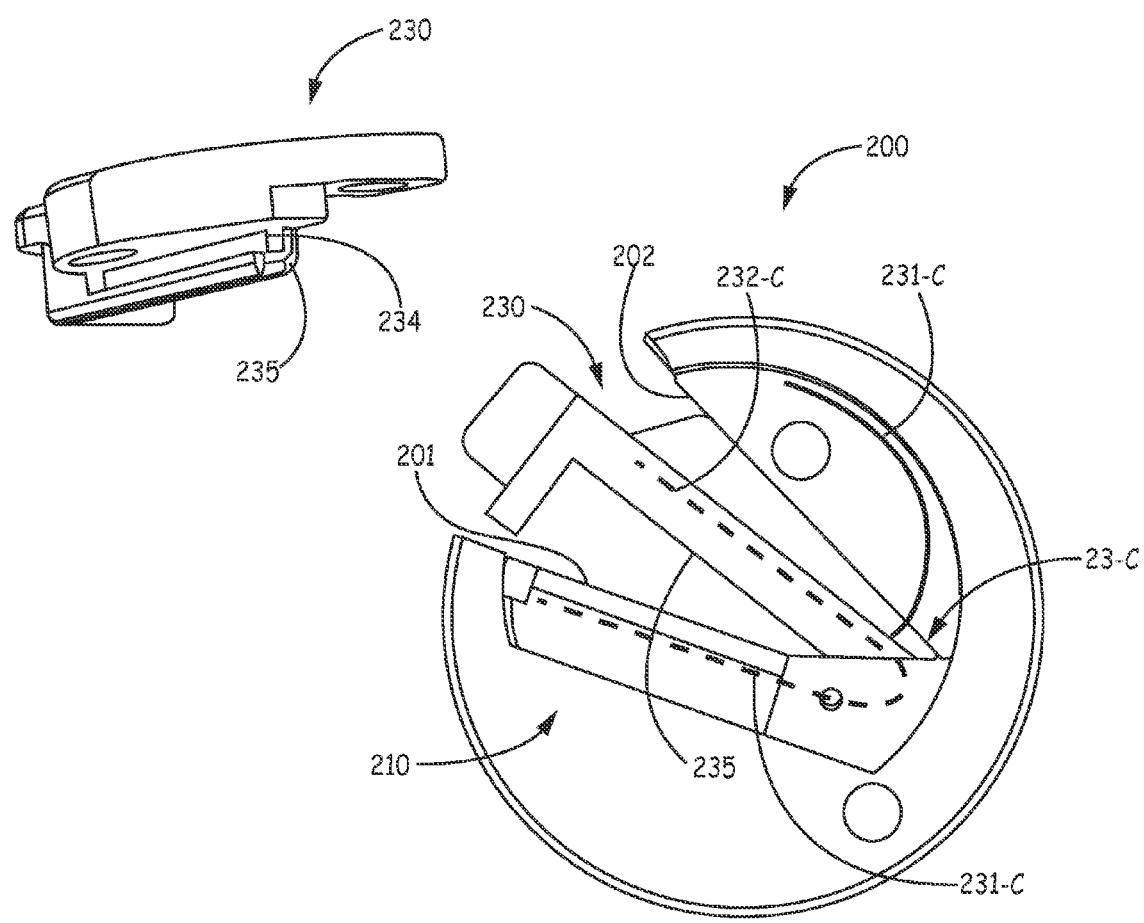
FIG. 3C is a perspective view of a portion of the anchoring assembly of FIG. 3A, alongside a bottom plan view of the assembly, according to some alternate embodiments.

With further reference to FIG. 3B, securing element 230 includes an engagement surface 235 and a spring member 23-B, wherein spring member 23-B includes a first portion 231-B, which is fixed to post 215 of plate member 210, and a second, moveable, or flexing portion 232-B, which is coupled to engagement surface 235, via capture within a bulk of securing element 230, for example, via insert molding of securing element 230 around spring member 23-B. Or, with reference to FIG. 3C, securing element 230 may include a groove, or channel 234, which is formed behind engagement surface 235, to receive moveable portion 232-B of spring member 23-B, or, according to an alternate embodiment, to receive a moveable portion 232-C of a clip type spring member 23-C. With reference to the bottom plan view of FIG. 3C, two possible configurations of spring member 23-C are shown. In a first configuration, a fixed portion 231-C of spring member 23-C is received in a channel of plate member 210, which is located behind second side 202 of slot 213, such that moveable portion 232-C is biased away from fixed portion 231-C, to move engagement surface 235 into the closed position. In a second configuration, fixed portion 231-C is received in a channel of plate member 210, which is located behind first side 201 of slot 213, such that moveable portion 232-C is biased toward fixed portion 231-C, to move engagement surface 235 into the closed position. Either of spring members 23-B, 23-C may be formed from a biocompatible metal of suitable elasticity, for example, stainless steel, or, preferably, nitinol, for MRI compatibility. FIG. 3A shows engagement surface 235 of securing element 230 in an open position, extending at an angle with respect to side 201 of slot 213, and spaced apart from slot side 201 by a distance that allows insertion of an elongate medical device into slot 213, via opening 203, for example, a proximal portion of implanted lead 15 that extends proximally out from a body portal (e.g., cranial burr hole 11). According to the illustrated embodiment, moveable portion 232-B, 232-C of spring member 23-B, 23-C of securing element 230 is held in the open position, against the bias thereof, by a retaining member, for example, a first pin member of a pair of pin members included in a retaining tool 270 shown in FIG. 3D.

With further reference to FIGS. 3A-B, the first pin member of the pair of pin members is sized to pass through a hole 27 of securing element 230 and an underlying hole 217 of plate member 210, while a second pin member of the pair is sized to pass through a second hole 219 of plate member 210. Thus, the retaining member formed by the pair of pin members, for example, included in tool 270 of FIG. 3D, both engages securing element 230 relative to plate member 210, via holes 27 and 217, to hold engagement surface 235 in the open position, and simultaneously engages plate member 210, via hole 219, to hold an entirety of assembly 200 and move assembly 200 into position over a body portal, for example, burr hole 11. FIG. 3D illustrates retaining tool 270 engaged with anchoring assembly 200 to move anchoring assembly 200 over burr hole 11, per arrow P, wherein burr hole 11 is fitted with a base ring 212, and has a proximal portion of an implanted lead 15 extending out therefrom. A recessed mounting surface 24 of base ring 212 is shown having an inner perimeter that defines a hole 240, which is generally aligned with burr hole 11, when fitted around burr hole 11, for example, by means of a base ring fitting tool 500, which is described below in conjunction with FIGS. 3F-H. According to the illustrated embodiment, the proximal portion of lead 15 is inserted through opening 203 of slot 213 as tool 270 moves assembly 200 into position over burr hole 11, per arrow P. It should be noted that any of the alternate base ring embodiments, which are described below, in conjunction with FIGS. 5D-E, may be included in assembly 200 as a substitute for base ring 212.

Figure 3E:
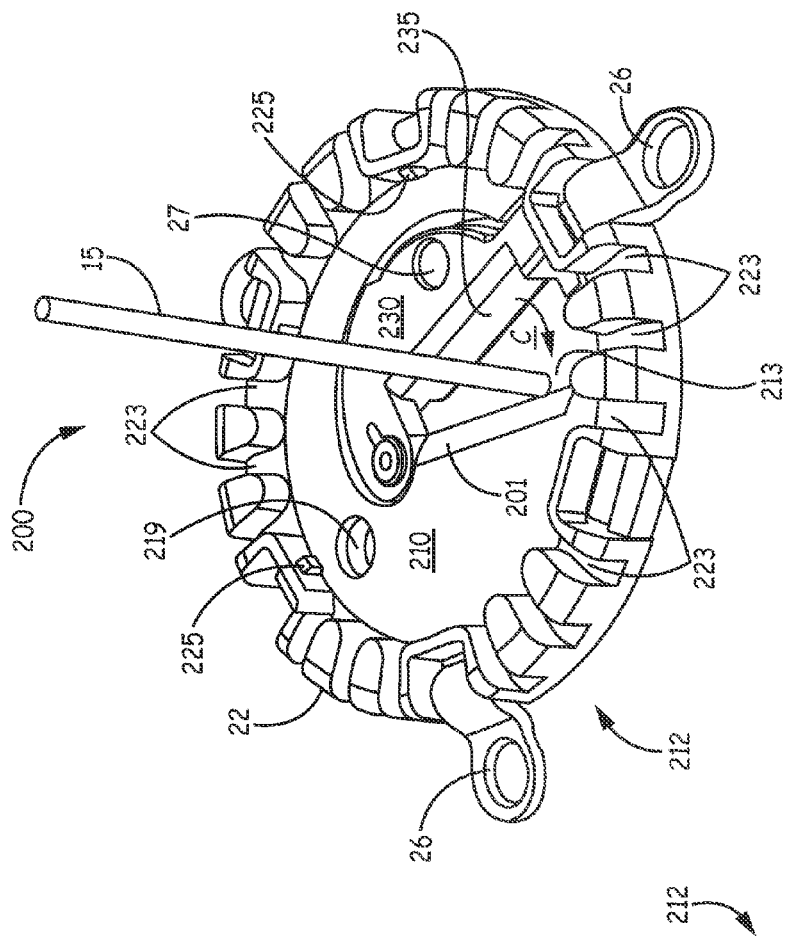
FIG. 3E is a perspective view of the anchoring assembly including the base ring, according to some embodiments.
Figure 3D:
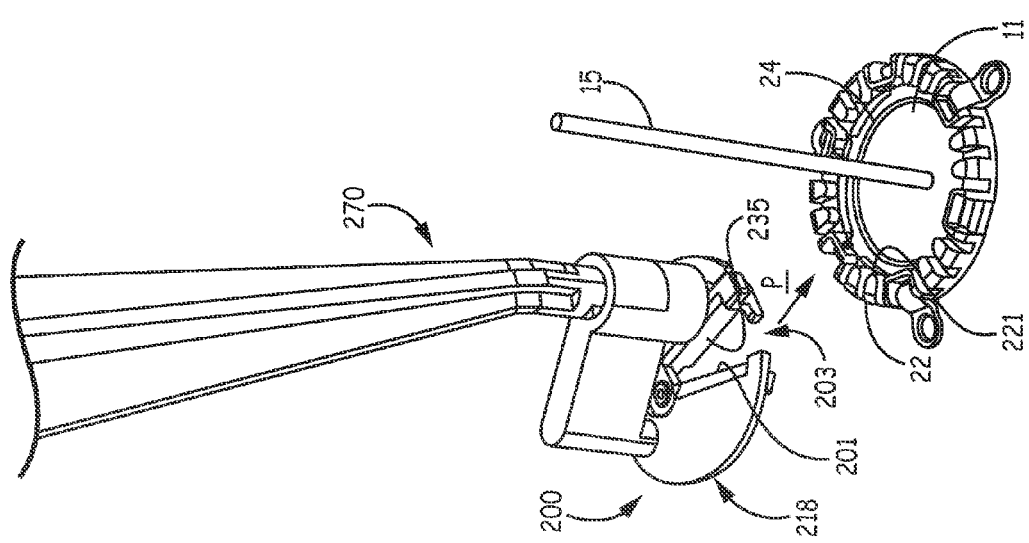
FIG. 3D is a perspective view of a retaining member engaged with the anchoring assembly of FIGS. 3A-B, alongside a base ring, which may form part of the assembly, according to some embodiments.

With reference to FIG. 3E, base ring 212 forms a part of assembly 200, according to some embodiments, when plate 210 is fitted within an inner perimeter surface 221 of a rim 22 of base ring 212 so that a lower surface 218 of plate member 210 abuts recessed mounting surface 24 of base ring 212. FIG. 3E illustrates such a fit of plate member 210, wherein plate member 210 is engaged in a snap-fit by snap-fit features 225 that protrude from inner perimeter surface 221. FIG. 3E further illustrates the retaining member of tool 270 disengaged from securing element 230 and plate 210 to allow engagement surface 235 to move, per arrow C into the closed position for the anchoring of lead 15. According to some embodiments, securing element 230 includes an end portion 233, best seen in FIG. 3A, which is configured to engage beneath a shoulder 211 of plate member 210, when engagement surface 235 is in the closed position, to prevent securing member 230 from moving out of the defined plane of plate member 210. FIG. 3A further illustrates securing element 230 including an end surface 236 that abuts a facing surface of shoulder 211 when element 230 is in the closed position, thereby maintaining a minimum and approximately uniform gap between engagement surface 235 and first side 201 of slot 213, to prevent pinching of the anchored lead 15.

With further reference to FIG. 3E, base ring 212 includes fastening elements 26 having holes to receive fasteners therethrough, for example, screws that secure base ring 212 to a skull around a perimeter of burr hole 11. According to a preferred embodiment, fastening elements 26 are flexible, or can pivot relative to a remainder of ring 212 to conform to various sizes of skulls. An upper surface of rim 22 of base ring 212 is shown having a plurality of channels 223 formed therein, each of which is sized to receive a proximal portion of anchored lead 15 that extends out from burr hole 11, so that one of channels 223 may be selected to guide the routing of lead 15 in an appropriate direction away from burr hole 11. Base ring 212 may be formed, for example, by molding, from a biocompatible polymer such as polyurethane, polycarbonate, polysulfone, PEEK, or nylon.

Figure 3G:
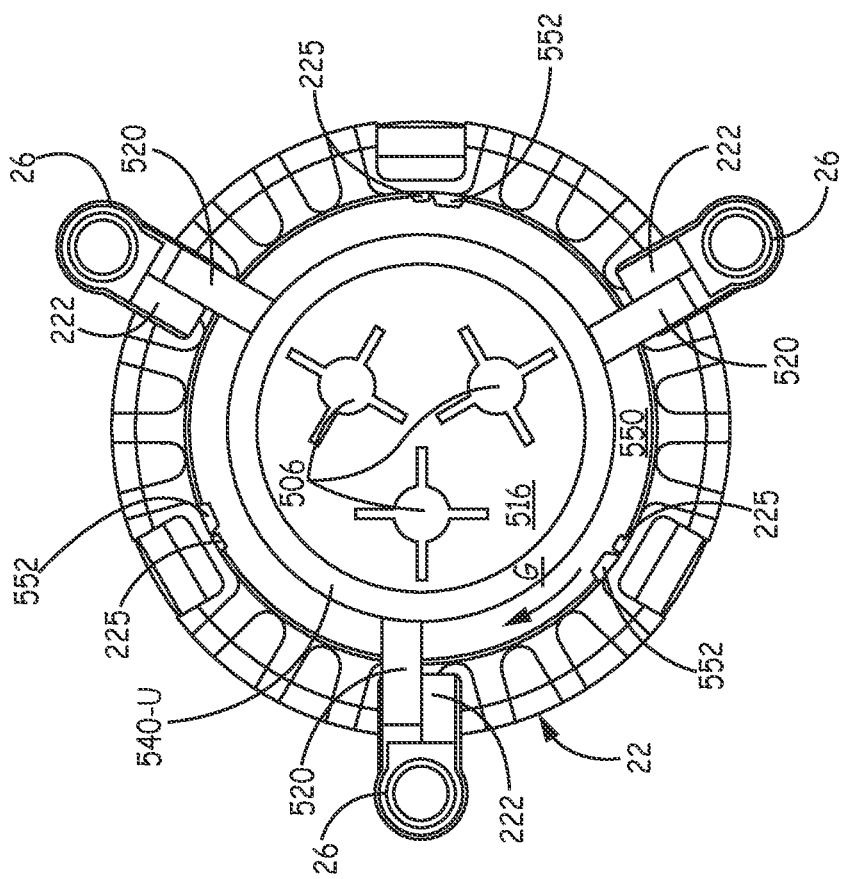
FIG. 3G is a top plan view of the assembly of the base ring centering tool coupled to the base ring, according to some embodiments.
Figure 3F:
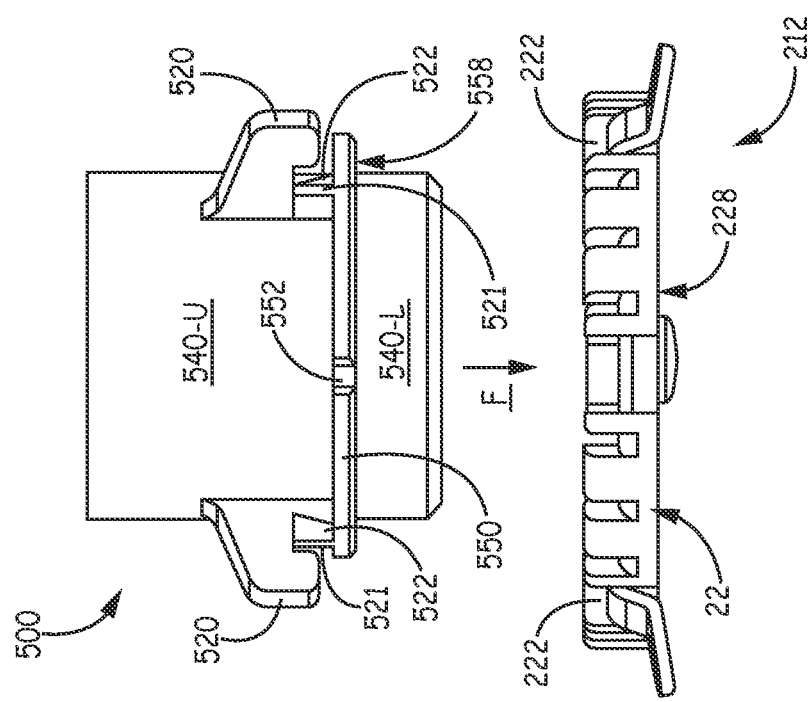
FIG. 3F is an elevation view of the base ring portion of the assembly shown in FIG. 3E and further including a base ring centering tool, according to some embodiments.

FIG. 3F is an elevation view of base ring centering tool 500, alluded to above, positioned adjacent base ring 212, for coupling thereto, and FIG. 3G is a top plan view of base ring centering tool 500 coupled to base ring 212, according to some embodiments. FIG. 3F illustrates centering tool 500 including a barrel having an upper portion 540-U and a lower portion 540-L, and clip arms 520, which extend outward from upper portion 540-U of barrel, and are spaced apart from one another about a perimeter of the barrel. FIG. 3F further illustrates centering tool 500 including a collar 550 that extends around the perimeter of the barrel, between upper portion 540-U and lower portion 540-L, wherein collar 550 includes slots 552 extending through a thickness thereof. With reference to FIG. 3G, it may be seen that slots 552 are spaced apart from one another about the perimeter of the barrel. FIG. 3G further illustrates a plurality of receptacles 506, for example, tabbed cut-outs, formed in an upper surface 516 of tool 500. Each receptacle 506 is configured to temporarily secure a fastener, while tool 500 is fitting base ring 212 around burr hole 11, after which each fastener is taken from the corresponding receptacle 506 and engaged with a corresponding fastening element 26 to secure the fitted base ring 212 in place.

According to the illustrated embodiment, after properly orienting tool 500 relative to base ring 200, as shown, with slots 552 of collar 500 aligned with snap fit features 225 (FIG. 3E) of base ring 212, and clip arms 520 aligned with recessed wall portions 222 of rim 22 of base ring 212, centering tool 500 is coupled to base ring 212 by inserting lower portion 540-L of the barrel thereof through hole 240 (FIG. 3D) of base ring 212, per arrow F, so that each clip arm 520 grasps around the corresponding wall portion 222 (best seen in FIG. 3H), each snap fit feature 225 has passed through a corresponding slot 552, a lower portion 540-L protrudes from a lower surface 228 of base ring 212 (FIG. 3H), and a lower surface 558 of collar 550 of tool 500 abuts mounting surface 24 (FIG. 3D) of base ring 212. Then, tool 500 is rotated relative base ring 212, per arrow G of FIG. 3G, so that collar 550 of tool 500 slides between snap-fit features 225 and mounting surface 24 of base ring 212. With reference to FIG. 3G, snap fit features 225 are seen offset from slots 552 as a result of the rotation per arrow G.

Figure 3H:
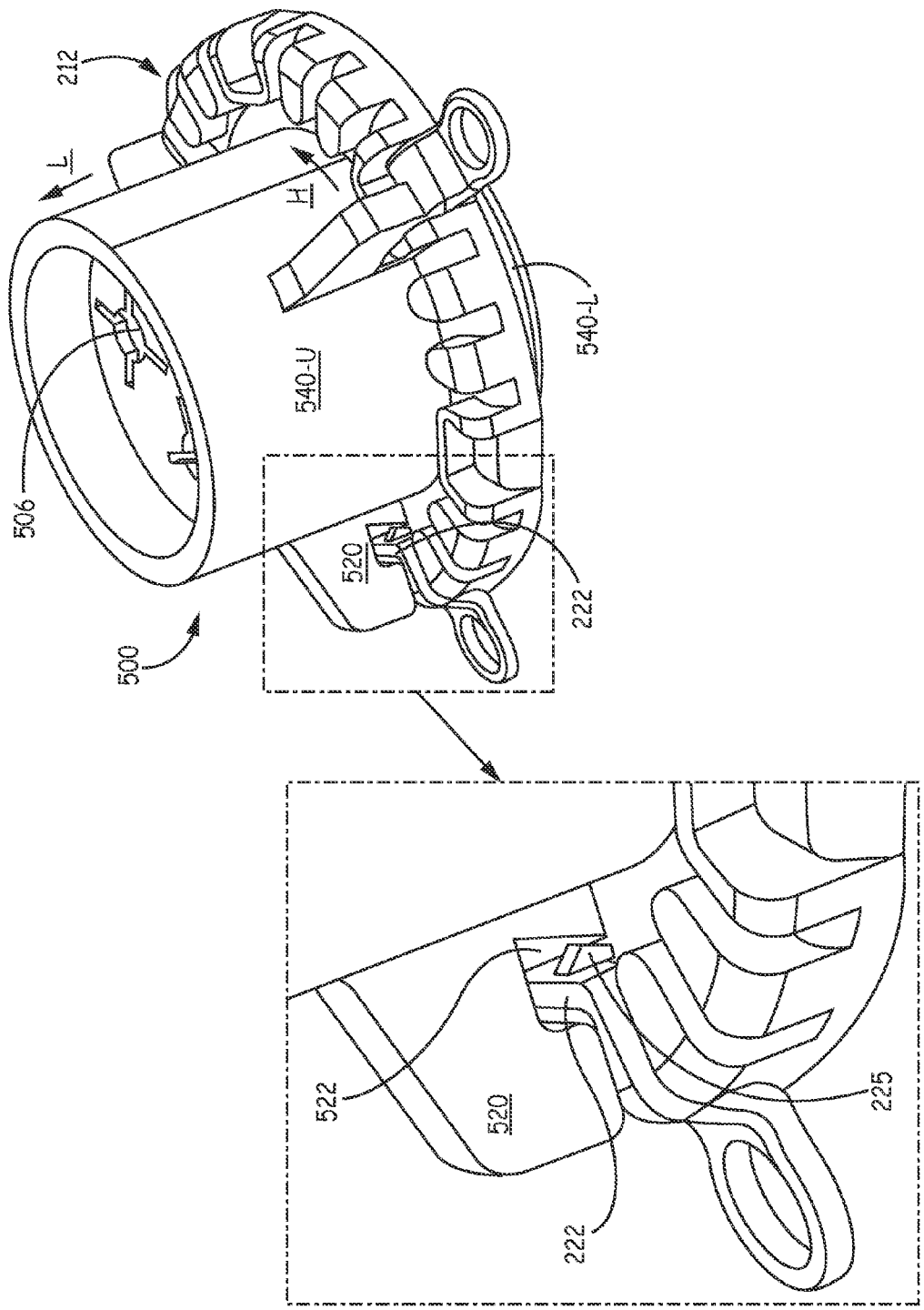
FIG. 3H is a perspective view, with an enlarged detail view, of the assembly of FIG. 3G, according to some embodiments.

With further reference to FIG. 3F, tool 500 further includes a protruding tab member located beneath each clip arm 520, wherein each tab member includes a peak surface 521 and a ramp surface 522 receding therefrom. When lower portion 540-L of the barrel of tool 500 is inserted through hole 240 of base ring 212, per arrow F, each peak surface 521 engages a corresponding snap-fit feature 225, on each wall portion 222, in a press fit that compresses the snap fit features 225; and, then, when tool 500 is rotated, per arrow G of FIG. 3G, each receding ramp surface 522 relieves the press-fit engagement between the corresponding peak surface 521 and snap-fit feature 225, for example, as illustrated in FIG. 3H. FIG. 3H is a perspective view, with an enlarged detail view, of tool 500 coupled to base ring 212, according to some embodiments. With reference to FIG. 3H, one of snap-fit features 225 is shown adjacent ramped surface 522 of the corresponding tab member of tool 500, when tool 500 is coupled to base ring 212 for positioning base ring 212 around burr hole 11. After positioning base ring 212, tool 500 is rotated, per arrow H, relative to base ring 212, so that tool 500 can be lifted away from base ring 212, per arrow L. The rotation per arrow H realigns each slot 552 of collar 550 with the corresponding snap-fit feature 225 of base ring 212, and compresses each snap-fit feature 225 (located on a wall portion 222 of base ring 212), via engagement with peak surface 521 of the corresponding tab member, which engagement is facilitated by each ramped surface 522.

Figure 4A:
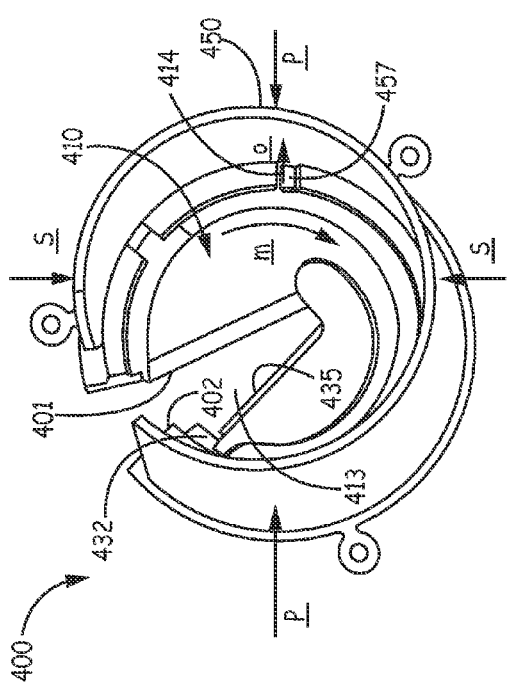
FIG. 4A is a perspective view of an anchoring assembly, according to yet further embodiments.
Figure 4B:
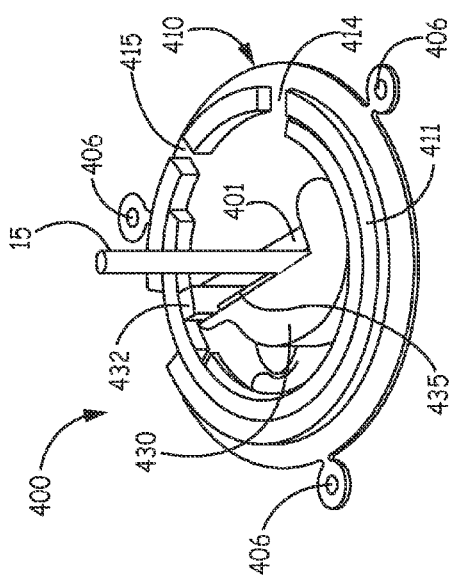
FIG. 4B is a perspective view a retaining member engaged with the anchoring assembly of FIG. 4A, according to some embodiments.
Figure 4C:
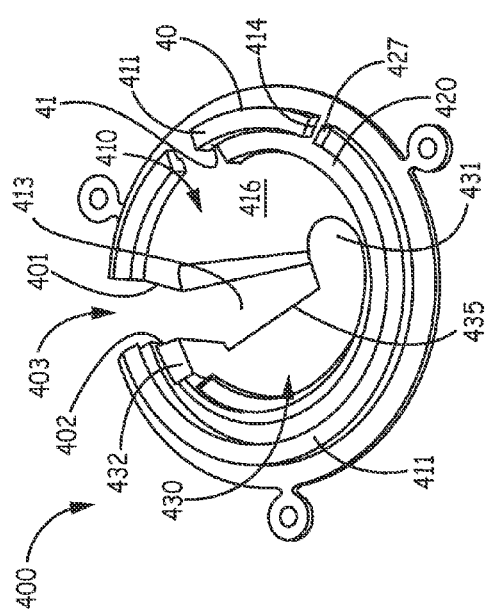
FIG. 4C is another perspective view in which an opposite side of the anchoring assembly of FIG. 4A is shown.

FIGS. 4A-D are various perspective views of an anchoring assembly 400, according to yet further embodiments. FIGS. 4A-B illustrates assembly 400 including a plate member 410, generally defining a plane, and a securing element 430, which is pivotably attached thereto; securing element 430 includes an engagement surface 435, which extends between first and second ends 431, 432 thereof, and a spring member 43, which may be seen in FIG. 4C. FIG. 4C illustrates spring member 43 including a first portion 441, which is fixed to plate member 410, for example, being secured in a bulk of a plug portion 48 of assembly 400 that extends from a lower surface 418 of plate member 410, and a second, flexing or moveable portion 442, which is coupled to engagement surface 435, for example, being captured within a bulk of securing element 430 at first end 431 thereof. FIGS. 4A-B further illustrate plate member 410 including a slot 413, which extends generally along the defined plane of plate member 410, and an outer perimeter ridge 411, which protrudes from an upper surface 416 of plate member 410. Slot 413 includes opposing sides 401, 402, which extend from an opening 403 of slot 413, located at a perimeter of plate member 410, and ridge 411 extends from a first end thereof, in proximity to side 401 of slot 413, to a second end thereof, in proximity to side 402 of slot 413. Plate member 410 may be formed, for example, by molding, from a biocompatible polymer such as polyurethane, polysulfone, PEEK, or nylon. Securing element 430 may be formed, for example, by insert molding any of the aforementioned a biocompatible polymers around moveable portion 442 of spring member 43. Spring member 43 may be formed from a biocompatible metal of suitable elasticity, for example, stainless steel, or, preferably, nitinol, for MRI compatibility.

Figure 4D:
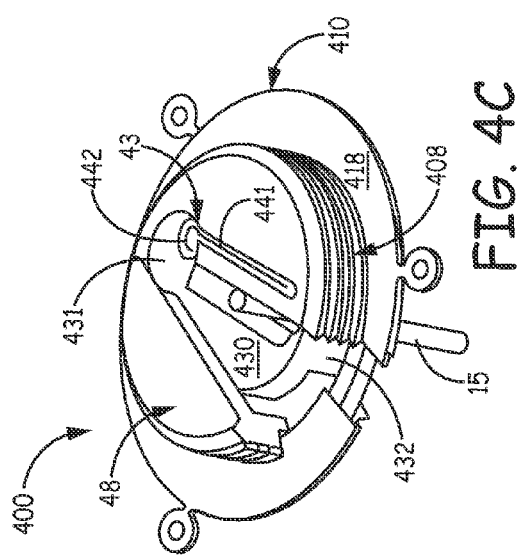
FIG. 4D is yet another perspective view of the anchoring assembly of FIG. 4A, according to some embodiments.

According to the illustrated embodiment, spring member 43 attaches securing element 430 to plate member 410 and is spring biased to move engagement surface 435 from an open position shown in FIGS. 4A-B, to a closed position shown in FIGS. 4C-D. FIG. 4B illustrates assembly 400 further including a removable outer retaining member 450, which is fitted around outer perimeter ridge 411, to hold engagement surface 435 in the open position, by engaging moveable portion 442 of spring member 43 against the bias thereof, via an inward projecting tab 457 of retaining member 450 that engages with a latch feature 427 attached to securing element 430 (FIG. 4A), as will be described in greater detail below. Outer retaining member 450 may be formed, for example, by molding, from a biocompatible polymer such as polyurethane, polysulfone, PEEK, or nylon.

With further reference to FIGS. 4A-B, ridge 411 includes a gap 414 formed therein that extends therethrough, from an inner surface 41 thereof to an outer surface 40 thereof. According to the illustrated embodiment, an inner ring 420, which is fitted against inner surface 41 of ridge 411, and attached to second end 432 of securing element 430, acts with retaining member 450 to hold engagement surface 435 in the open position. As seen in FIG. 4A, latch feature 427 of ring 420 projects outward into gap 414 so that, when outer retaining member 450 is fitted around ridge 411, as shown in FIG. 4B, inward projecting tab 457 of outer retaining member 450 engages latch feature 457, thereby engaging securing element 430 and holding engagement surface 435 in the open position. Inner ring 420 may be formed, for example, by molding, from any of the aforementioned biocompatible polymers (i.e. polyurethane, polysulfone, PEEK, nylon).

After inserting a proximal portion of implanted lead 15 into slot 413, via opening 403, and fitting assembly 400 into a body portal, for example, by press fitting plug portion 48 of plate member 410 (FIG. 4C) into the portal, inner ring 420 may be released from engagement with outer retaining member 450 so that moveable portion 442 of spring member 43 is released to move engagement surface 435 of securing element 430 into the closed position, where engagement surface 435 anchors lead 15 against first side 401 of slot 413, as shown in FIGS. 4C-D. With further reference to FIG. 4B, according to some embodiments and methods, the press fit of plug portion 48, which may include press fit features 408 defining an outer perimeter thereof, according to FIG. 4C, may be accomplished by squeezing opposing sides of outer retaining member 450, for example, per arrows P, to compress the outer perimeter of plug portion 48 for insertion into the body portal. Furthermore, according to some embodiments, outer retaining member 450 is deformable with respect to ridge 411 of plate 410, so that the release of inner ring 420 may also be accomplished by squeezing opposing sides of outer retaining member 450, per arrows S, as follows. Squeezing outer retaining member 450, per arrows S, deforms the wall of member 450 to move inward projecting tab 457 out from gap 414 of ridge 411, per arrow o, and disengages tab 457 from outward projecting latch feature 427 of inner ring 420, so that inner ring 420 is allowed to slide, per arrow m, in response to the bias of spring member 43, thereby moving engagement surface 435 of securing element 430 to the closed position shown in FIGS. 4C-D, after which retaining member 450 may be removed from around ridge 411. FIGS. 4C-D illustrate a protrusion of second end 432 of securing element 430 relative to engagement surface 435 (also seen in FIGS. 4A-B), which serves to limit a minimum distance between engagement surface 435 and first side 401 of slot 413, at the closed position, and thereby prevents 'over-pinching' of lead 15, that may cause damage thereto.

FIG. 4D further illustrates ridge 411 including another gap 415 similar to, and spaced apart from the above described gap 414, according to some embodiments. Once implanted lead 15 is anchored between engagement surface 435 and first side 401 of slot 413, the portion of lead 15 that extends proximally from the anchored portion may be routed through one of gaps 414, 415, for example, prior to securing a cap over assembly 400. Gaps 414, 415 may be sized to grip lead 15, when routed therethrough. A suitable cap for assembly 400 may have features that interlock with ridge 411 to secure the cap in place. Furthermore, according to the illustrated embodiment, screws received through holes 406 may fasten anchoring assembly 400 to a skull in which the body portal is formed, after press fitting plug portion 48 therein.

FIGS. 4E-F are perspective views of an anchoring assembly 900 similar to, but simplified from anchoring assembly 400. FIG. 4E illustrates assembly 900 including a plate member 910 to which a spring-biased securing element 930 is coupled via a post 919 at a first end 931 thereof, such that element 930 is pivotable thereabout in a direction approximately parallel to a plane that is generally defined by plate 910. A spring member (not shown) of securing element 930 may be integrated into anchoring assembly 900 in a manner similar to that described above for spring member 23-B or 23-C of anchoring assembly 200; and securing element 930 overlays a surface 916 of plate member 910, in a fashion similar to that described above for securing element 230 of assembly 200. FIG. 4E shows an engagement surface 935 of securing element 930 in a spring biased closed position, relative to a first side 901 of a slot 913 formed in plate member 910, at which engagement surface 935 may anchor an elongate medical device, like lead 15, against first side 901 of slot 913 (similar to engagement surface 435 of assembly 400). FIG. 4F illustrates assembly 900 including a removable retaining member 950 fitted about a perimeter ridge 911 of plate 910, such that a tab 957 of a deformable portion 955 of member 950 engages second end 932 of securing element 930 to hold engagement surface 935 in an open position, against the spring bias, so that the device, for example, lead 15, can be inserted into slot 913.

According to the illustrated embodiment, when deformable portion 955 of retaining member 950 is pivoted outward, per arrow O, relative to the remainder of member 950, for example, about a junction 953 thereof, tab 957 is disengaged from second end 932 of element 930, thereby allowing engagement surface 935 to move into the spring biased closed position. Like assembly 400, retaining member 950 may be squeezed to compress the outer perimeter of a plug portion (not shown, but similar to that of assembly 400) of assembly 900 for insertion into the body portal, after inserting lead 15 into slot 913, and before disengaging tab 957 of member 950, after which member 950 may be removed from around ridge 911. With further reference to FIGS. 4E-F, perimeter ridge 911 of plate member 910 includes an internal groove 921, which is located in proximity to side 901 of slot 913, and second end 932 of securing element has a tab formed therein, which is configured to engage within groove 921, as shown in FIG. 4E. The engagement of second end 932 of securing element 930 within groove 921 helps to prevent movement of second end 932 out of the defined plane of plate member 910, when engagement surface 935 is in the closed position.

Figures 1A, 1B:
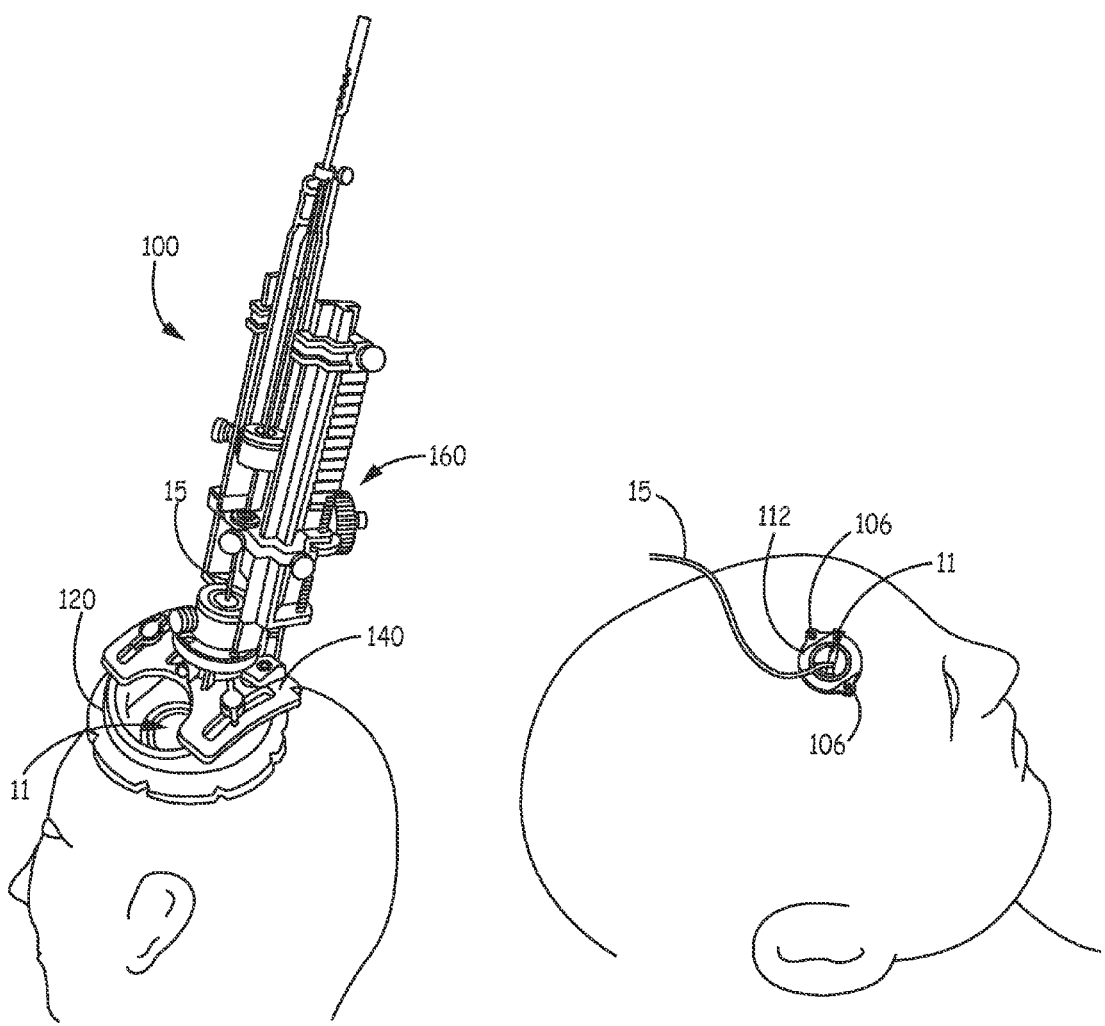
FIG. 1A is a perspective view of an exemplary stereotactic guidance mounted to a patient's skull.
FIG. 1B shows an exemplary base ring mounted in a burr hole of the skull.

FIGS. 5A-B are perspective views of an anchoring assembly 600, according to some alternate embodiments. FIG. 5A illustrates assembly 600 including a plate member 610, which generally defines a plane, and a securing element 630, which is pivotably attached to an upper surface 616 of plate member 610, for example by mounting features 2, to rotate between an open position, at which securing element 630 extends at an angle with respect to the defined plane, and a closed position, at which securing element 630 extends approximately parallel to the defined plane. Assembly 600 may further include a base ring in which plate member 610 is fitted, for example, similar to base ring 112 that lines burr hole 11 (FIG. 1B), or base ring 212, described above, or a base ring 612 that is described below in conjunction with FIGS. 5D-E. Optional detent features 61, which are shown extending from a lower surface 618 of plate 610, may engage with an inner perimeter of the base ring (112, 612) to hold assembly 600 in place within the body portal. FIG. 5A further illustrates plate member 610 including a slot 613 having opposing sides 601, 602, which extend generally along the defined plane of plate member 610 from a slot opening 603, at a perimeter of plate member 610. Plate member 610 and securing element 630 may each be formed, for example, by molding, from a biocompatible polymer such as polyurethane, polycarbonate, polysulfone, polyether ether ketone (PEEK), or nylon.

FIGS. 5A-B illustrates securing element 630 in the open position, wherein an engagement surface 635 thereof extends in proximity to side 602 of slot 613 and is spaced apart from first side 601 of slot so that an elongate medical device, for example, a portion of implanted lead 15 that extends proximally out from the body portal, can be inserted into slot 613, via opening 603, for example, prior to fitting assembly 600 into any of the aforementioned base rings 112, 212, 612. After inserting lead 15 into slot 613, securing element 630 may be rotated toward upper surface 616 of plate 610, per arrow C, to lift engagement surface 635 into the closed position, for example, as shown in FIG. 5C, at which engagement surface 635 is in closer proximity to side 601 of slot 613, and holds lead 15 against first side 601 to anchor lead 15 in the body portal, for example, burr hole 11. According to some embodiments, a groove (not shown) is formed along a length of engagement surface 635, that is, approximately orthogonal to the extent of lead 15 shown in FIGS. 5A-C, for example, to provide a pair of higher pressure gripping areas for holding lead 15 against first side 601 of slot 613. Alternately, or in addition, engagement surface 635 may be roughened or textured, for example, knurled, to enhance gripping. First side 601 of slot 613 may likewise be grooved and/or textured.

With further reference to FIGS. 5A-C, securing element 630 includes a latching portion 632, which may be configured to engage with plate member 610 to secure element 630 in the closed position that is illustrated in FIG. 5C. However, according to some embodiments, a base ring includes features to engage with and secure element 630 in the closed position. For example, as illustrated in FIG. 5D, base ring 612 (or an insert thereof) includes one or more detent-like features 68 that form a rim extending from upper surface 616 of plate member 610, when plate member 610 is fitted within ring 612; each feature 68 includes an inward-facing cam arm 683 configured to engage latching portion 632 of securing element 630, when securing element 630 is moved into the closed position. Features 68 may further be configured to engage plate member 610, thereby holding assembly 600 over the body portal. FIG. 5D further illustrates each detent-like feature 68 including an outward facing cam arm 689 configured to secure a cap 69, which is shown in FIG. 5E, over assembly 600 and anchored implanted lead 15. Cap 69 may be formed from any of the aforementioned polymer materials (i.e. polyurethane, polycarbonate, polysulfone, PEEK, nylon), or from a relatively low durometer biocompatible polymer, for example, silicone rubber or a lower durometer grade of polyurethane. According to the illustrated embodiment, the proximal portion of the implanted and anchored lead 15 may be routed through any of a plurality of channels that are created by gaps 685 between adjacent features 685, and, once the proximal portion is positioned in the selected gap 685, cap 69 may be secured in place so that the proximal portion passes through an exit port 695 thereof, for example, as illustrated in FIG. 5E. It should be noted that both of engagement surface 635 and first side 601 of slot 613 preferably have rounded edges at upper surface 616 of plate 610 to prevent undue stress concentration on lead 15 when bent over upper surface 616 for routing beneath cap 69.

According to some preferred embodiments, the illustrated plurality of detent-like features 68 are formed in a ring member insert that is separate from a bulk of base ring 612 (that part which includes fastening elements 606 to receive screws/bone fasteners), and the ring member insert is more rigid than the bulk of base ring 612, for example, which may be formed from silicone rubber, or a relatively low durometer polyurethane, or any of the aforementioned polymer materials (i.e. polyurethane, polycarbonate, polysulfone, PEEK, nylon). The ring member insert may be formed, for example, by screw machine manufacture, from a biocompatible metal, such as a stainless steel alloy, or, preferably, nitinol, for MRI compatibility, but may alternately be formed from any of the relatively rigid aforementioned polymer materials. A more flexible bulk of base ring 612 can allow fastening elements 606 to conform to various sizes of skulls.

In the foregoing detailed description, the invention has been described with reference to specific embodiments and methods. However, it may be appreciated that various modifications and changes can be made without departing from the scope of the invention as set forth in the appended claims.

The invention claimed is:

1. An anchoring assembly for an elongate medical device, the assembly comprising:
   a plate member generally defining a plane and including a slot that extends generally along the plane, the slot including a first side, a second side, opposite the first side, and an opening located at a perimeter of the plate member, from which the first and second sides extend;
   a securing element attached to the plate member and overlaying a surface of the plate member, the surface being substantially parallel to the defined plane of the plate member, the securing element including an engagement surface and a spring member, the spring member including a first portion fixed to the plate member, and a second, moveable portion coupled to the engagement surface to move the engagement surface, relative to the plate member, between an open position and a closed position, the engagement surface being spaced apart from the first side of the slot by a first distance in the open position, and being spaced apart from the first side of the slot by a second distance in the closed position, the first distance allowing insertion of the elongate medical device through the opening of the slot and between the engagement surface and the first side of the slot, and the second distance being less than the first distance at which the engagement surface anchors the inserted device; and
   a retaining member comprising a first pin member configured to engage and disengage with the securing element, and a second pin member configured to engage and disengage with the plate member;
   wherein the retaining member, when engaged with the securing element, holds the moveable portion of the spring member against a bias of the spring member, to keep the engagement surface of the securing element in the open position; and
   when the retaining member is disengaged from the securing element, the moveable portion of the spring member is released to move the engagement surface to the closed position.

2. The assembly of claim 1, wherein the engagement surface of the securing element, in the open position, extends at an angle with respect to the first side of the slot of the plate member; and when the moveable portion of the spring member is released, the engagement surface pivots through the angle toward the first side of the slot.

3. The assembly of claim 2, wherein the first side of the slot of the plate member includes a shoulder formed therein at the perimeter of the plate member; and the securing element further includes an end portion located in proximity to the opening of the slot, the end portion being configured to engage beneath the shoulder of the first side of the slot, when the engagement surface of the securing element is in the closed position.

4. The assembly of claim 1, wherein:
   the plate member further includes a hole extending therethrough;
   the securing element includes a hole formed therethrough, the hole of the securing element aligned with the hole of the plate member when the engagement surface is in the open position; and
   wherein the first pin member is sized to simultaneously fit within the holes of the plate member and the securing element to hold the engagement surface of the securing element in the open position, and the first pin member is removable from the holes to allow the engagement surface of the securing element to move to the closed position.

5. The assembly of claim 4, wherein:
   the hole of the plate member is a first hole of a pair of holes extending through the plate member, a second hole of the pair of holes being spaced apart from the first hole by a distance; and
   wherein the second pin member is spaced apart from the first pin member by approximately the same distance by which the first and second holes of the plate member are spaced apart, the second pin member being sized to fit within the second hole, when the first pin member fits within the first hole to hold the engagement surface of the securing element in the open position, and the second pin member being removable from the second hole along with the first pin member being removable from the first hole to allow the engagement surface of the securing element to move to the closed position.

6. The assembly of claim 1, further comprising a base ring to fit around a body portal, the base ring including a rim and a mounting surface, the mounting surface having an inner perimeter that defines a hole to be aligned with the body portal, the mounting surface extending within an inner perimeter surface of the rim and being recessed from an upper surface of the rim; wherein the plate member fits within the inner perimeter surface of the rim with a lower surface of the plate member abutting the mounting surface of the base ring, the lower surface being opposite the surface of the plate member which is overlaid by the securing element.

7. The assembly of claim 6, wherein:
the rim of the base ring includes snap-fit features protruding inward from the inner perimeter surface thereof; and
when the lower surface of the plate member abuts the mounting surface of the base ring, the snap-fit features of the rim engage the plate member in a snap fit.

8. The assembly of claim 7, wherein
the upper surface of the rim includes a plurality of grooves formed therein, each groove extending from the inner perimeter surface of the rim outward; and
when the plate member is engaged in the snap fit, one of the grooves is located to receive a proximal portion of the inserted device.

9. The assembly of claim 6, wherein the base ring is separate from a remainder of the assembly, and further comprising a base ring centering tool for fitting the base ring around the body portal before fitting the plate member within the inner perimeter surface of the rim of the base ring; the base ring centering tool comprising:
a barrel including an upper portion and a lower portion, a perimeter of the lower portion being sized to fit through the hole of the base ring and within the body portal; and
a plurality of clip arms extending outward from the upper portion of the barrel and spaced apart from one another about the perimeter of the upper portion, each clip arm being configured to grasp around a wall portion of the rim of the base ring when the lower portion of the barrel extends through the hole of the base ring and protrudes from a lower surface thereof, the lower surface being opposite the mounting surface.

10. The assembly of claim 9, wherein:
the rim of the base ring includes snap-fit features protruding inward from the inner perimeter surface thereof;
the base ring centering tool further comprises a collar extending about a perimeter thereof, between the upper portion and the lower portion, the collar having a lower surface and slots extending through a thickness thereof, each slot being located for alignment with a corresponding snap-fit feature as the lower portion of the barrel of the centering tool is inserted through the hole of the base ring so that the lower surface of the collar abuts the mounting surface of the base ring, and the thickness of the collar allows the collar to slide between the snap-fit features of the base ring and the mounting surface of the base ring when the lower surface of the collar abuts the mounting surface.

11. The assembly of claim 10, wherein:
at least one of the snap-fit features is located on one of the wall portions of the rim that is engaged by one of the clip arms of the base centering tool;
the upper portion of the base ring centering tool further includes a protruding tab member located beneath each clip arm, each protruding tab member including a peak surface and a ramp surface receding from the peak surface, the peak surface engaging a corresponding snap-fit feature as the lower portion of the barrel of the centering tool is inserted through the hole of the base ring, and, when the lower surface of the collar abuts the mounting surface and as the tool is rotated so that the collar slides between the snap-fit features and the mounting surface, the ramp surface of each tab member of the tool relieves the engagement between the peak surface of each tab member.

12. The assembly of claim 9, wherein the upper portion of the barrel of the base ring centering tool includes at least one receptacle formed in an upper surface thereof, the at least one receptacle configured to temporarily secure at least one fastener, the at least one fastener being configured to secure the fitted base ring in place around the body portal.

* * * * *